(12) United States Patent
Bonetti et al.

(10) Patent No.: US 8,664,395 B2
(45) Date of Patent: Mar. 4, 2014

(54) PURIFICATION 4-AZA-ANDROST-1-ENE-17-OIC ACID FROM 4-AZA-ANDROSTAN-17-OIC ACID

(75) Inventors: Mauro Bonetti, Udine (IT); Sabrina De Rosa, Udine (IT)

(73) Assignee: PHF S.A., Lugano (CH)

( * ) Notice: Subject to any disclaimer, the term of this patent is extended or adjusted under 35 U.S.C. 154(b) by 281 days.

(21) Appl. No.: 13/257,865

(22) PCT Filed: Apr. 2, 2009

(86) PCT No.: PCT/EP2009/053972
§ 371 (c)(1),
(2), (4) Date: Sep. 20, 2011

(87) PCT Pub. No.: WO2010/112079
PCT Pub. Date: Oct. 7, 2010

(65) Prior Publication Data
US 2012/0029196 A1   Feb. 2, 2012

(51) Int. Cl.
*C07D 221/18* (2006.01)
*A61K 31/435* (2006.01)

(52) U.S. Cl.
USPC .......................................... 546/77; 514/284

(58) Field of Classification Search
USPC ............................................ 546/77; 514/284
See application file for complete search history.

(56) References Cited

U.S. PATENT DOCUMENTS

2005/0059692 A1   3/2005 Reddy et al.

OTHER PUBLICATIONS

K. Satyanarayana et al., "A Scaleable Synthesis of Dutasteride: A Selective 5.alpha.-Reductase Inhibitor," *Organic Process Research and Development*, American Chemical Society, vol. 11, No. 5, Sep. 21, 2007, pp. 842-845.
K. Satyanarayana et al., "Impurity profile study of dutasteride," *Pharmazie*, 62(10), 743-746 CODEN: PHARAT; ISSN: 0031-7144, 2007, p. 743, col. 2, paragraph 2.1 Scheme 1: p. 744, col. 2, paragraph 2.5.
K. P. Zhang et al., "Synthesis of dutasteride," *Journal of Chinese Pharmaceutical Sciences*, Beijing, vol. 16, No. 3, Jan. 1, 2007, pp. 233-235.

*Primary Examiner* — Rita Desai
(74) *Attorney, Agent, or Firm* — Dickstein Shapiro LLP

(57) ABSTRACT

The present invention relates to a process of separation of 4-aza-androst-1-ene-17-oic acid from 4-aza-androstan-17-oic acid, which brings to 4-aza-androst-1-ene-17-oic containing less than 0.05% w/w of 4-aza-androstan-17-oic acid, with high yield and productivity. In particular, the present invention relates to a process for the separation of 4-aza-androstan-17-oic acid from 4-aza-androst-1-ene-17-oic acid, comprising the steps of treating the crude 4-aza-androst-1-ene-17-oic acid with formic acid and recovering the purified 4-aza-androst-1-ene-17-oic acid containing 4-aza-androstan-17-oic acid in w/w % less than 0.05%.

10 Claims, No Drawings

PURIFICATION 4-AZA-ANDROST-1-ENE-17-OIC ACID FROM 4-AZA-ANDROSTAN-17-OIC ACID

FIELD OF THE INVENTION

The present invention relates to a process of separation of 4-aza-androst-1-ene-17-oic acid from 4-aza-androstan-17-oic acid, which brings to 4-aza-androst-1-ene-17-oic containing less than 0.1% w/w of 4-aza-androstan-17-oic acid, with high yield and productivity.

BACKGROUND ART

Dihydrodutasteride (Formula 1)

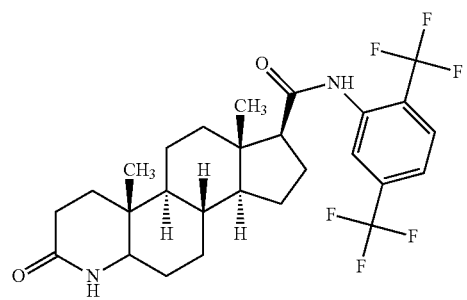

Formula 1 is one of the impurities which is hard to eliminate from Dutasteride (Formula 2)

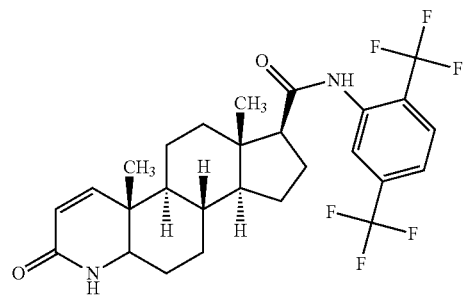

Formula 2

The International patent application published under WO27120263 describes how to purify Dutasteride, derived from Dihydrodutasteride, from Desmethyldutasteride (Formula 3)

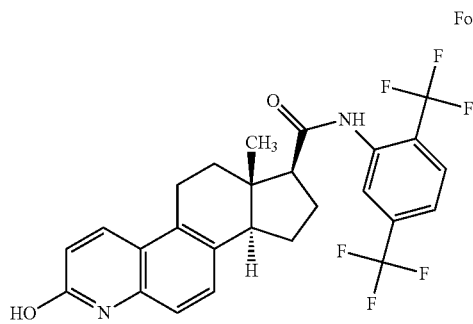

Formula 3 and from other unknown impurities which are normally present. According to this patent application, unknown impurities and Desmethyldutasteride can be eliminated through common separation techniques. In particular, unknown impurities can be removed through digestion of solid Dutasteride in mixtures of acetonitrile and hydrochloric acid, while Desmethyldutasteride is eliminated through crystallization of Dutasteride from mixtures of tetrahydrofuran/water. The purification to remove Dihydrodutasteride is done through chromatografic methods, which are difficult to be used at large scale.

No examples of separation of Dihydrodutasteride from Dutasteride through crystallization are published in the literature.

The patent application published under WO2007120263 describes also that the content of Dihydrodutasteride in the brand product from the originator, Avodart, is 0.12% with respect to Dutasteride, near to the ICH limit for non qualified impurities. This means that Dihydrodutasteride is typical of the manufacturing process of Dutasteride.

Several manufacturing processes for Dutasteride are described in the literature and in a lot of patents. They can be divided into two classes.

The first one describes the amidation reaction of 4-aza-androst-1-ene-17-oic acid (hereafter called Intermediate 1), activated on the carboxylic —COX group with 2,5-bis trifluoromethyl aniline:

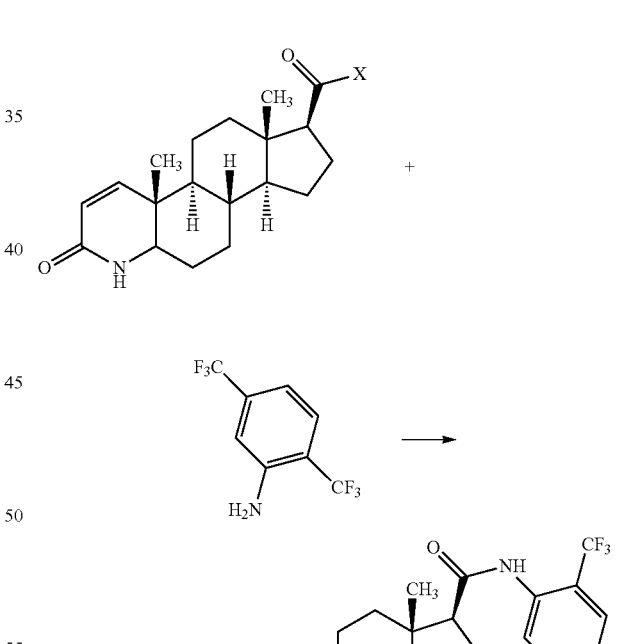

In the same class of prior art, the patent application published under WO9507927 describes the activation of the carboxylic moiety with thionyl chloride, while the patent application published under WO2008101308 describes the activation with carbonyldiimidazole.

In the second class of prior art, Dihydrodutasteride is dehydrogenated:

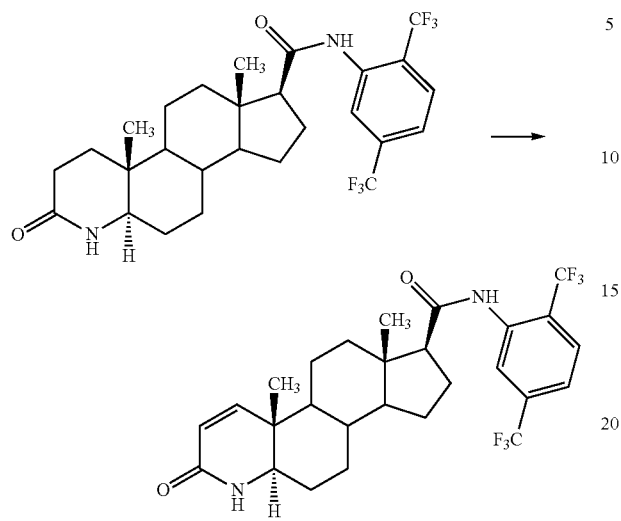

Examples of this reaction are described in several patents.

When the manufacturing process belongs to the second class of prior art, the presence of Dihydrodutasteride in the final Dutasteride derives from the starting material which has not reacted.

On the other hand, when the manufacturing process belongs to the first class of prior art described above, Dihydrodutasteride derives from 4-aza-androstan-17-oic acid (hereafter indicated as Intermediate 2 and also called "hydrogenated Intermediate 1"), impurity of Intermediate 1, which is a starting material of the synthesis, as Intermediate 1 comes from dehydrogenation of hydrogenated Intermediate 1.

Therefore there is the need of a synthetic method to obtain Dutasteride with a content of Dihydrodutasteride within ICH limits avoiding the use of purification techniques not applicable to large production scale.

The separation of Dihydrodutasteride from Dutasteride using the normal techniques of separation solid-liquid, is not possible because Dutasteride and Dihydrodutasteride together give solid solutions. Moreover Dihydrodutasteride has a melting point (256.0° C.) higher than Dutasteride (247.5° C.), so that an eventual crystallization increases the content of Dihydrodutasteride in the isolated product.

| MOLAR RATIO Dutasteride/Dihydrodutasteride | MELTING POINT, ° C. |
|---|---|
| 90:1 | 250.2 |
| 61:39 | 250.6 |
| 38:62 | 251.7 |
| 18:82 | 253.5 |

Therefore, it is not possible to purify Dutasteride from Dihydrodutasteride by means of crystallization when Dutasteride is synthesized from Dihydrodutasteride through dehydrogenation.

If Dutasteride is synthesized through amidation reaction from Intermediate 1, the only way to prepare the final product with a Dihydrodutasteride content within ICH limits is to use a starting material, Intermediate 1, with an adequate low level of hydrogenated Intermediate 1 (Intermediate 2).

DESCRIPTION OF THE INVENTION

The present invention relates to a process of separation of Intermediate 1 from Intermediate 2 (hydrogenated Intermediate 1), which brings to an Intermediate 1 containing less than 0.1% w/w of Intermediate 2, with high yields and productivity.

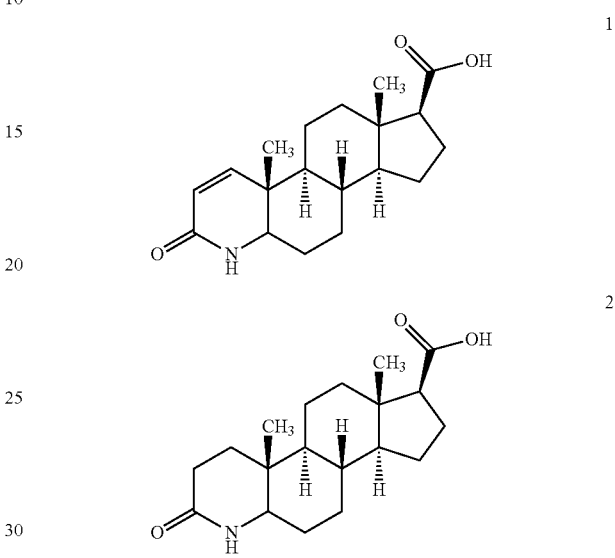

The Intermediate 1 containing Intermediate 2 (hydrogenated Intermediate 1), gives, after the process mentioned before, Dutasteride containing a certain amount of Dihydrodutasteride.

The purification through crystallization of a mixture of Intermediate 1 and Intermediate 2 by using conventional solvents is not possible because Intermediate 2 is normally less soluble than Intermediate 1.

| SOLVENT | solubility Intermediate 1 at 25° C., % w/w | solubility Intermediate 2 at 25° C., % w/w |
|---|---|---|
| Methanol | 0.6 | 0.16 |
| Ethyl acetate | 0.02 | 0.003 |
| Toluene | <LOD | <LOD |
| Methylene chloride | 0.04 | 0.008 |
| Acetone | 0.06 | 0.008 |
| DMF | 2.4 | 0.40 |
| MTBE | 0.009 | 0.001 |

(LOD = Limit Of Detection)

It was surprisingly found that the solubility of Intermediate 2 (hydrogenated Intermediate 1) in formic acid is higher than Intermediate 1, thus making the purification of Intermediate 1 from Intermediate 2 possible.

This fact is even more surprising because other similar carboxylic acid solvents, such as acetic acid and propionic acid, do not share the reversed solubility behaviour displayed by formic acid.

| SOLVENT | solubility Intermediate 1 at 25° C., % w/w | solubility hydrogenated Intermediate 1 at 25° C., % w/w |
|---|---|---|
| Formic Acid | 7.7 | 20.32 |
| Acetic Acid | 8.1 | 3.69 |
| Propionic Acid | 6.6 | 3.10 |

However, it was found that a conventional crystallization in formic acid can not be conducted, since the solubilisation of Intermediate 1 at specific concentrations requires high temperatures. In such conditions formic acid reacts with Intermediate 1 according to the following scheme:

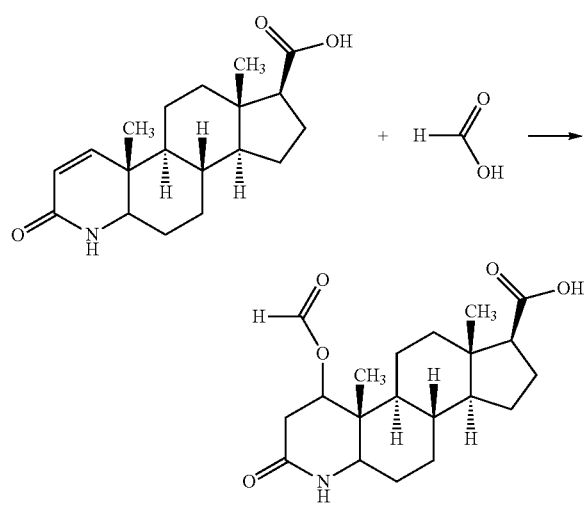

It was found however that, operating at low temperatures, the desired purification can be performed without dissolving and then re-precipitating Intermediate 1, but through a so called "digestion" of the product. In these conditions, no reaction with formic acid, as described above, occurs.

In practice, the solid is suspended in formic acid and kept for a certain time, preferably under stirring, until the impurity (Intermediate 2) dissolves.

In one embodiment, formic acid is used in w/w amounts ranging from 3 to 4 times the amount of crude Intermediate 1.

The treatment temperature is selected to be sufficiently low to avoid any reaction of formic acid onto Intermediate 1 scaffold. Preferably, the treatment temperature will be less than 40° C. In a further embodiment, the treatment temperature will be higher than −10° C. or higher than 0° C. and less than 35° C.

This operation can be done in one single purification step or in two steps. When the treatment is conducted in one step, it can be performed for a time above 20 hours, preferably above 25 hours, and less than 60 hours, preferably less than 50 hours. The same treatment times are applied for the overall digestion, when it is conducted in two steps.

When the treatment is performed in two steps, the mother liquors from the first step can also be used for the treatment of a new batch of Dutasteride, thus increasing the yield.

Moreover it was surprisingly found that, by using particular homogenising equipments which can break crystals (i.e. Ultra-Turrax®, a homogeniser from Ika), the desired result can be obtained in one single purification step and quickly. In this case, the treatment time can be in the range of from 3 to 22 hours, preferably from 4 to 18 hours.

Preferably, the homogeniser is used at a rotational speed of 4.000 to 6.000 rpm.

The methods described above have a high yield and are adequate to industrial production.

EXAMPLES

Example 1

Purification in Two Steps Recycling the Mother Liquors from the Second Stage 100 g of crude Intermediate 1, containing 0.63% of Intermediate 2 (hydrogenated Intermediate 1), was digested at 25° C. for 6 hours with 345 g of formic acid. The solid was filtered and washed with methanol on the filter. After drying it was obtained 73 g of the solid product, with a yield of 73%.

The full quantity so isolated was suspended in 263 g of formic acid and digested again for 16 hours. After filtration, washing with methanol on the filter and drying, 52.7 g of purified Intermediate 1 were obtained. The yield of the second digestion was 72.5%, so the overall yield of the process was 52.7%.

34.5 g of mother liquors coming from the second digestion were used to treat 10 g of crude Intermediate 1, containing 0.63% of Intermediate 2. After 24 hours of digestion, the solid was filtered, washed with methanol and dried, obtaining 10.5 g of a solid containing 0.11% of Intermediate 2. The yield of this first purification was 105%.

Then the product was digested again, with a yield of 70% and a content of Intermediate 2 below 0.05%. The overall yield was 73%.

Example 2

Purification Under Stirring by Ultra Turrax®

A reactor of 250 ml equipped with an Ultra Turrax® 50 was charged with 70 g of Intermediate 1 containing 0.63% of Intermediate 2 and 241 g of formic acid. The suspension was digested for 5 hours at a stirring speed of 5000 rpm at 20° C. After filtration, washing with methanol and drying 48.5 g of purified Intermediate 1 were obtained, with a content of Intermediate 2 of 0.08%. The yield was 69%.

Example 3

Purification Under Stirring by Ultra Turrax®

The experiment in Example 2 was repeated with a digesting time of 15 hours instead of 5 hours. 52.2 g of purified Intermediate 1 were obtained, with a content of Intermediate 2 of 0.09%. The yield was 75%.

Example 4

Purification in One Step 15 g of crude Intermediate 1, containing 0.63% of hydrogenated Intermediate 1, were digested at 25° C. for hours with 52 g of formic acid. The solid was filtered and washed with methanol on the filter. After drying the weight of the solid product obtained was 10.7 g, with a yield of 71%. The content of Intermediate 2 was 0.07%.

Example 5

Purification in One Step

The experiment in Example 4 was repeated with a digesting time of 48 hours instead of 32 hours. 10.8 g were obtained, with a yield of 72%. The content of Intermediate 2 was 0.06%.

Example 6

Preparation of Dutasteride Starting from the Intermediate 1 Obtained in Example 1

A reactor of 0.5 l equipped with a mechanical stirrer, a condenser, a thermometer, a dropping funnel and a heating bath at 25° C. was charged with 40 g of Intermediate 1 containing 0.04% of Intermediate 2, 1044 g of toluene, 40 g of pyridine. To the suspension obtained, kept at 0° C., a solution containing 18 g of thionyl chloride in 29 g of toluene was added in about 40 minutes, through the dropping funnel. The reaction mass was kept under stirring at 18° C. for about 4 hours. Then, 0.31 g of dimethylamminopyridine and 29 g of 2,5-bis(trifluoromethyl)aniline were added. The reaction mass was heated at 110° C. for about 20 hours, then cooled at 25° C. Then the suspension was filtered through a filter of sinterized glass G4 and washed with 600 ml of ethyl acetate. The organic phases were put together and washed in the reactor at 50° C. under stirring with 10% KOH (2×256 ml), 10% HCl (1×256 ml) and water (1×256 ml). Then the organic phase was concentrated under vacuum at 50° C. 160 g of acetonitrile were added to the concentrated residue and the mixture was refluxed until complete dissolution of the solid. The solution was cooled at 0° C., the crystallized solid was filtered on a filter of sinterized glass G4, washed with acetonitrile (3×15 ml) and dried in an oven under vacuum at 70° C. for about 8 hours. 38 g of white solid Dutasteride were obtained, with an HPLC purity of 99.5% and a Dihydrodutasteride content of 0.07%.

Example 7

Preparation of Dutasteride Starting from the Intermediate 1 Obtained in Example 2

A reactor of 0.5 l equipped with a mechanical stirrer, a condenser, a thermometer, a dropping funnel and a heating bath at 25° C. was charged with 5 g of Intermediate 1 containing 0.09% of Intermediate 2, 130 g of toluene, 5 g of pyridine. To the suspension obtained, kept at 0° C., a solution containing 2.2 g of thionyl chloride in 3.6 g of toluene was added in about 40 minutes, through the dropping funnel. The reaction mass was kept under stirring at 18° C. for about 5 hours. Then, 0.04 g of dimethylaminopyridine and 3.7 g of 2,5-bis(trifluoromethyl)aniline were added. The reaction mass was heated at 110° for about 20 hours, then cooled at 25° C. Then the suspension was filtered through a filter of sinterized glass G4 and washed with 600 ml of ethyl acetate. The organic phases were put together and washed in the reactor at 50° C. under stirring with 10% KOH (2×32 ml), 10% HCl (1×32 ml), and water (1×32 ml). Then the organic phase was concentrated under vacuum at 50° C. 20 g of acetonitrile were added to the concentrated residue and the mixture was refluxed until complete dissolution of the solid. The solution was cooled at 0° C., the crystallized solid was filtered on a filter of sinterized glass G4, washed with acetonitrile (3×2.5 ml) and dried in an oven under vacuum at 70° C. for about 8 hours. 3 g of white solid Dutasteride were obtained, with an HPLC purity of 99.6% and a Dihydrodutasteride content of 0.12%.

The invention claimed is:

1. Process for the separation of 4-aza-androstan-17-oic acid from 4-aza-androst-1-ene-17-oic acid, comprising the steps of treating the crude 4-aza-androst-1-ene-17-oic acid with formic acid and recovering the purified 4-aza-androst-1-ene-17-oic acid containing 4-aza-androstan-17-oic acid in w/w % less than 0.05%.

2. Process according to claim 1, wherein the said treatment is made under stirring at a treatment temperature less than 40° C.

3. Process according to claim 2, wherein the said treatment is made at a treatment temperature higher than −10° C. or higher than 0° C. and less than 35° C.

4. Process according to claim 1, wherein the duration of the treatment is more than 4 hours.

5. Process according to claim 4, wherein the duration of the treatment is above 20 hours or above 25 hours, and less than 60 hours or less than 50 hours.

6. Process according to claim 1, wherein the treatment with formic acid is performed under stirring by means of an homogeniser.

7. Process according to claim 6, wherein the said homogenizer operates at a rotational speed of from 4000 to 6000 rpm.

8. Process according to claim 6, wherein the treatment time is in the range of from 3 to 22 hours, or from 4 to 18 hours.

9. Process according to claim 1, wherein the treatment is performed in two steps.

10. Process according to claim 1, wherein formic acid is used in w/w amounts ranging from 3 to 4 times the amount of crude 4-aza-androst-1-ene-17-oic acid.

* * * * *